US006940067B2

(12) United States Patent
Nakashige et al.

(10) Patent No.: US 6,940,067 B2
(45) Date of Patent: Sep. 6, 2005

(54) HAZARDOUS MATERIAL DETECTION SYSTEM

(75) Inventors: Keiko Nakashige, Hitachi (JP); Seiji Tanaka, Hitachinaka (JP); Hiroyuki Fujita, Hitachiota (JP); Toshio Iwasaki, Hitachi (JP); Yoshihiro Nishikawa, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/886,620

(22) Filed: Jul. 9, 2004

(65) Prior Publication Data

US 2004/0245449 A1 Dec. 9, 2004

Related U.S. Application Data

(63) Continuation of application No. 10/465,586, filed on Jun. 20, 2003, now Pat. No. 6,806,450.

(30) Foreign Application Priority Data

Jun. 24, 2002 (JP) ........................................ 2002-182847

(51) Int. Cl.[7] ............................................... H01J 49/10
(52) U.S. Cl. ..................................................... 250/288
(58) Field of Search ................................. 250/288, 281, 250/282

(56) References Cited

U.S. PATENT DOCUMENTS

| | | | |
|---|---|---|---|
| 4,820,920 A | 4/1989 | Bather | |
| 4,849,628 A | 7/1989 | McLuckey et al. | |
| 5,162,652 A | 11/1992 | Cohen et al. | |
| 5,425,263 A | 6/1995 | Davies et al. | |
| 5,465,607 A | 11/1995 | Corrigan et al. | |
| 6,571,649 B2 | 6/2003 | Sakairi et al. | |
| 6,806,450 B2 * | 10/2004 | Nakashige et al. | 250/288 |
| 2001/0042413 A1 | 11/2001 | Sakairi et al. | |
| 2002/0190201 A1 | 12/2002 | Yamada et al. | |
| 2003/0136902 A1 * | 7/2003 | Nakashige et al. | 250/282 |

FOREIGN PATENT DOCUMENTS

| | | |
|---|---|---|
| EP | 1 093151 | 4/2001 |
| JP | 6-310090 | 11/1994 |
| JP | 10-125276 | 5/1998 |

* cited by examiner

*Primary Examiner*—Kiet T Nguyen
(74) *Attorney, Agent, or Firm*—Mattingly, Stanger, Malur & Brundidge, P.C.

(57) ABSTRACT

A hazardous material detection system that can suppress occurrence of contamination due to ionization. When a sensor detects that a test sample has entered an inspection region of an X-ray inspection device as a belt conveyor moves, a corona discharge power supply in a hazardous material detection device is turned on for a constant time, to introduce a gaseous sample containing a substance stuck to the test sample into the hazardous material detection device via a sucking section and gaseous sample introduction piping, in order to ionize the gaseous sample and analyze it at an analyzer, based on a result of which analysis, a data processor decides whether the gaseous sample contains a hazardous material, to display a decision result on a screen. When the test sample is detected by an exit side sensor, the corona discharge power supply is turned off.

20 Claims, 7 Drawing Sheets

HAZARDOUS MATERIAL DETECTION SYSTEM

This is a continuation of U.S. Ser. No. 10/465,586, filed Jun. 20, 2003, now U.S. Pat. No. 6,806,450.

BACKGROUND OF THE INVENTION

The invention relates to a hazardous material detection system and, more particularly, to a hazardous material detection system well suited for use in detection of nitro compounds etc. that have a nitro group having a low saturated vapor pressure.

At an airport and other public facilities, it is attempted to install a hazardous material detection system that detects a nitro compound having a nitro group as a hazardous material, to prevent it from being brought into the airplane or a building. In this kind of hazardous material detection system, an atmospheric pressure ionization mass spectrometer is employed which is provided with an ion source operable at the atmospheric pressure, to analyze mass of a gaseous sample (gas to be inspected) containing a substance stuck to an incomer to be detected.

The atmospheric pressure ionization mass spectrometer introduces the gaseous sample to a corona discharge section fitted with a corona discharge needle electrode and an extraction electrode, applies a high voltage between the needle electrode and the extraction electrode to give rise to corona discharge in order to ionize the gaseous sample, introduces the ioned gaseous sample to an analysis section to analyze its mass, and outputs an analysis result to a data processor. The data processor is arranged to decide whether the gaseous sample contains the hazardous material based on the analysis result from the atmospheric pressure ionization mass spectrometer and output a result of the decision.

When it is analyzed by the atmospheric pressure ionization mass spectrometer, the gaseous sample introduced to the corona discharge section may contain non-polar to highly polar substances contained in the atmosphere as well as a dust ($SiO_2$) and an organic substance. Furthermore, introduced the gaseous sample contains a variety of miscellaneous substances including those having a low evaporation temperature through a high evaporation temperature. When the variety of substances contained in the gaseous sample is introduced to the corona discharge section, an inside of the ion source is contaminated and foreign matter such as silicon (Si) and carbon (C) sticks to the needle electrode and the extraction electrode. When the foreign matter sticks to the needle electrode and the extraction electrode, corona discharge becomes unstable, to deteriorate an ionization efficiency of a sample component as well. Especially if much foreign matter sticks to them, the gaseous sample cannot pass through pores in the corona discharge section, thereby disabling analysis. Therefore it becomes necessary to clean the needle electrode and the extraction electrode, thereby requiring additional time and labor.

To prevent contamination and clogging in the ion source, such a method has been proposed that, as described in Jpn. Pat. Appln. KOKAI Publication No. Hei 6-310090 and Jpn. Pat. Appln. KOKAI Publication No. Hei 10-125276, a liquid chromatograph mass spectrometer is provided with a pore electrode cleaner, to spray a washing solvent such as methanol, acetone, or water every constant time, thereby washing the pore electrode.

The method employed in the conventional technology of using such a washing solvent as acetone, methanol, or water to wash the needle electrode and the extraction electrode cannot sufficiently remove Si and C stuck to these needle electrode and extraction electrode. Moreover, the conventional technology can be applied to the liquid chromatograph mass spectrometer but not to an atmospheric pressure ionization mass spectrometer, which analyzes mass of the gaseous sample. Further, when such washing solvent as methanol, acetone, or water is used to wash the electrodes, the inside of the ion source section, which is heated to 200° C., is cooled down in a moment of time, thereby generating a cold spot. This causes in some cases sticking of dusts and organic substances in the gaseous sample, thereby clogging the pores.

That is, the conventional technology takes into account only washing the needle electrode and the extraction electrode if the inside of the ion source section is contaminated in connection with corona discharge but not suppressing occurrence of contamination due to ionization.

SUMMARY OF THE INVENTION

It is an object of the invention to provide a hazardous material detection system that can suppress occurrence of contamination due to ionization.

To solve these problems, the invention provides a hazardous material detection system comprising: gaseous sample introduction means for introducing a gaseous sample containing a substance stuck to a detection object; ionization means for ionizing the gaseous sample introduced by the gaseous sample introduction means, in response to an instruction; mass analysis means for analyzing mass of the gaseous sample ionized by the ionization means; and decision means for deciding whether the gaseous sample contains a hazardous material, based on an analysis result from the mass analysis means, wherein the ionization means ionizes the gaseous sample only for a time specified by the instruction.

In arrangement of the hazardous material detection system, as the gaseous sample introduction means, such means can be used as to introduce in response to an instruction a gaseous sample containing a substance stuck to a detection object, while as the ionization means, such means can be used as to ionize the introduced gaseous sample only if the gaseous sample has been introduced by the gaseous sample introduction means and, otherwise, stop ionization of the introduced gaseous sample.

Further, as the gaseous sample introduction means, such means can be used as to introduce a gaseous sample containing a substance stuck to a detection object from an inside of a detection object conveyance path which serves to manage entrance and exit of the detection object and also it can be provided with detection object detection means which outputs a detection signal when the detection object is in a detection region of the detection object conveyance path, while as the ionization means, such means can be used as to ionize a gaseous sample introduced by the gaseous sample introduction means in response to the detection signal. In this case, the ionization means can be arranged to ionize the gaseous sample only for a set time in response to the detection signal.

In arrangement of the hazardous material detection systems, various components can be added as follow.

(1) The gaseous sample introduction means is provided with a main path for introducing the gaseous sample from the detection object to the ionization means and a bypass path which discharges the gaseous sample from the detection object as bypassing the ionization means, wherein a flow rate of the gaseous sample passing through the bypass path is set larger than a flow rate of the gaseous sample passing through the main path.

(2) A filter unit for collecting dusts and organic substances contained in a fluid flowing through the main path is mounted to the main path on an upstream side of the ionization means.

Further, in arrangement of the hazardous material detection systems, alarm generation means can be provided which detects a voltage and a current of at least one of the pair of electrodes of the ionization means and, if at least one of the detected values exceeds a set value, generates an alarm to notify that a quantity of contamination generated due to ionization has exceeded a set value.

By the means, a gaseous sample is ionized only when necessary, so that occurrence of contamination due to ionization can be suppressed more effectively than in the case of ionizing the gaseous sample all the time, thereby prolonging a service life of a system.

Further, since the gaseous sample can be ionized for a prolonged time, it is possible to improve an accuracy, reproducibility, and a reliability of data obtained by mass analysis. When an alarm is generated also, it is possible to prompt cleaning of the electrodes of the ionization means.

Other objects, features and advantages of the invention will become apparent from the following description of the embodiments of the invention taken in conjunction with the accompanying drawings.

DETAILED DESCRIPTION OF THE INVENTION

Figure 1:
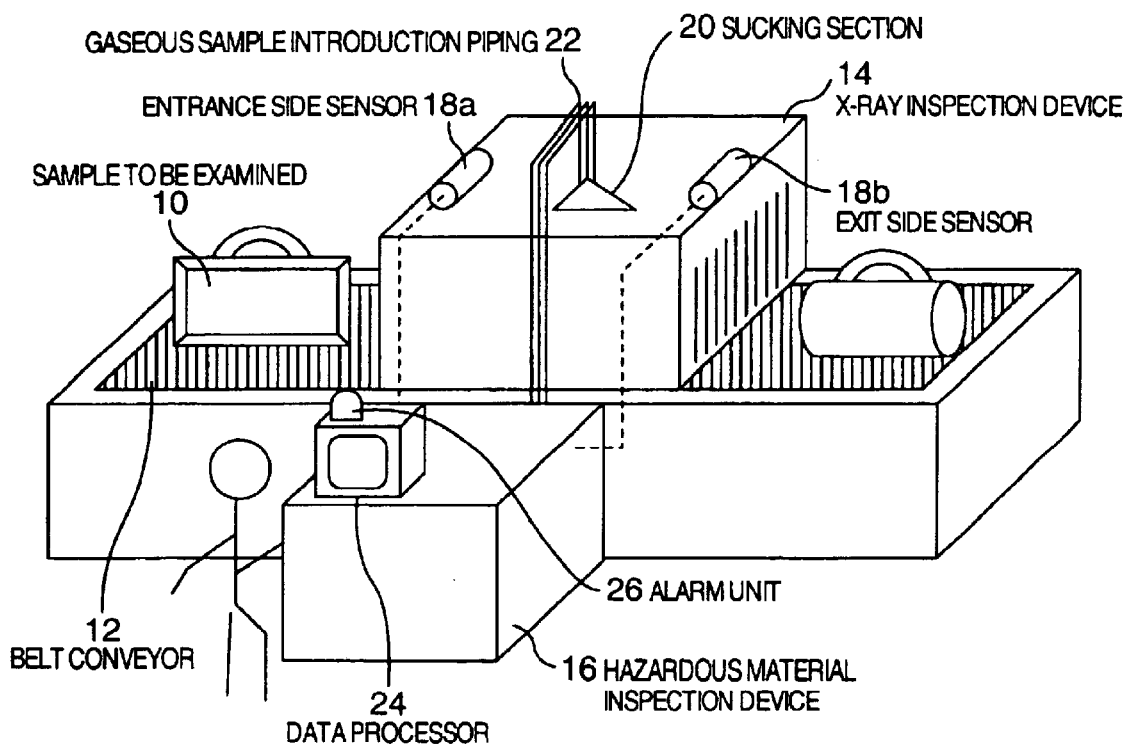
FIG. 1 is an overall configuration diagram of a hazardous material detection system according to a first embodiment of the invention.

The following will describe one embodiment of the invention with reference to drawings. FIG. 1 is an overall configuration diagram of a hazardous material detection system according to a first embodiment of the invention with which airports and public facilities are equipped. In FIG. 1, in the middle of a belt conveyor (detection object conveyance path) 12 which serves to monitor entrance and exit of a test sample 10 such as a bag as a detection object, there are arranged an X-ray inspection device 14 and a hazardous material detection device 16 adjacent to the X-ray inspection device 14. The X-ray inspection device 14 is provided with an entrance side sensor 18a to detect entrance of the test sample 10 into an X-ray inspection region of the X-ray inspection device 14 and an exit side sensor 18b to detect exit of the test sample 10 from the X-ray inspection region, in such a configuration that these sensors 18a and 18b are connected to the hazardous material detection device 16 via the respective cables. Further, at a center and on an upper side of the X-ray inspection device 14, there is arranged a conical suction section 20, an end of which suction section 20 is connected via gaseous sample introduction piping 22 to the hazardous material detection device 16. The suction section 20 is adapted to suck in a vapor of a gaseous sample containing a substance stuck to the test sample 10, for example, a hazardous material containing a nitro compound having a nitro group, which has a very low saturated vapor pressure and so is difficult to detect. The gaseous sample thus sucked in is supplied via the gaseous sample introduction piping 22 to the hazardous material detection device 16. That is, the suction section 20 and the gaseous sample introduction piping 22 are arranged as a constituent element of gaseous sample introduction means.

In the present embodiment, since the gaseous sample is introduced into the in source section 34 only for the time of inspection of the test sample 10, it is possible to more effectively suppress foreign matter contained in the gaseous sample from sticking to a needle electrode 44 or a extraction electrode 42, thereby prolonging a service life of each of the electrodes. Further, a corona discharge power supply 30 is turned on only for the time of inspection of the test sample 10, so that occurrence of contamination due to ionization can be suppressed more effectively than in the case of ionizing the gaseous sample all the time, thereby prolonging the service life of a system.

Figure 2:
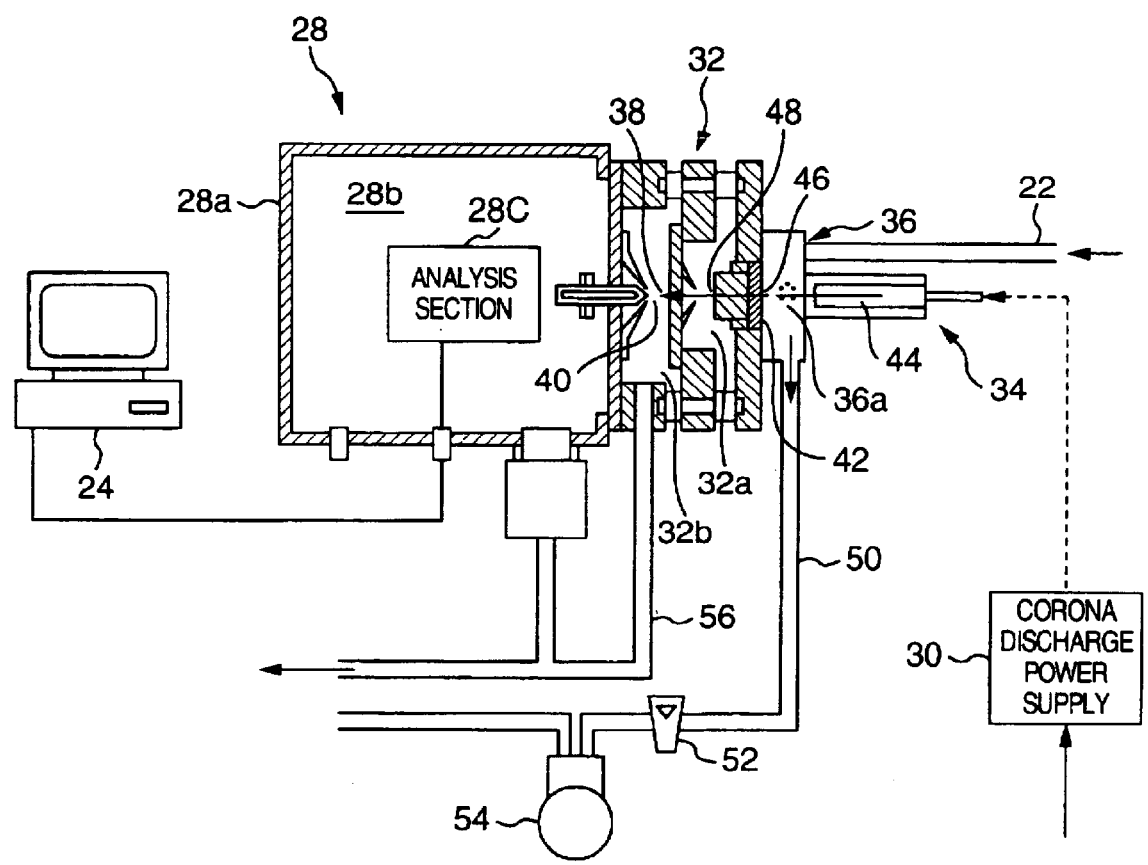
FIG. 2 is an important part cross-sectional configuration diagram of a hazardous material detection device.

Specifically, as shown in FIG. 2, the hazardous material detection device 16 comprises an analysis section 28, a corona discharge power supply 30, a differential exhaust section 32, an ion source section 34, a corona discharge section 36, etc., in such a configuration that the cables connected to the sensors 18a and 18b respectively are connected to the corona discharge power supply 30, while the gaseous sample introduction piping 22 is connected to the corona discharge section 36.

The analysis section 28 is provided with a vacuum vessel 28a whose an inside is constituted of a processing chamber 28b, in which an analyzer 28c connected to the data processor 24 is mounted. An inside of the differential exhaust section 32 arranged adjacent to the vacuum vessel 28a is divided into vacuum chambers 32a and 32b which are formed as two stages (front stage and rear stage), which are connected through piping 56 to an exhauster (not shown). In the differential exhaust section 32, the vacuum chambers 32a and 32b communicate with each other through a pore 38 and the rear stage side vacuum chamber 32b communicates with the processing chamber 28b through a pore 40.

On a partition wall of the front stage side vacuum chamber 32a of the differential exhaust section 32 is there provided the corona discharge section 36 in which a extraction electrode 42 and a needle electrode 44 are arranged as opposite to each other. A high voltage is applied between the extraction electrode 42 and the needle electrode 44 by the corona discharge power supply 30. For example, to ionize the gaseous sample (nitro group compound) by negative corona discharge, a negative DC voltage is applied between the electrodes 42 and 44. On the other hand, to ionize the gaseous sample (amino group compound) by positive corona discharge, a positive DC voltage is applied between the electrodes 42 and 44. Further, an inside of the corona discharge section 36 communicates with that of the differential exhaust section 32 via a pore 46 formed in the extraction electrode 42 and a pore 48 formed in the differential exhaust section 32. Furthermore, the corona discharge section 36 is connected to flow piping 50, in the middle of which a flow meter 52 and a gaseous sample introduction pump 54 are arranged. The gaseous sample introduction pump 54 is adapted to introduce the gaseous sample sent from the gaseous sample introduction piping 22 into the corona discharge section 36 and discharge this introduced gaseous sample through the flow piping 50. In this case, sucking force of the gaseous sample introduction pump 54 can be adjusted using the flow meter 52. That is, the flow piping 50, the flow meter 52, and the gaseous sample introduction pump 54 constitutes the gaseous sample introduction means together with the suction section 20 and the gaseous sample introduction piping 22.

The corona discharge section 36 is constituted as ionization means to ionize the gaseous sample by giving rise to corona discharge in a corona discharge region 36a in order to generate ions at the atmospheric pressure or a pressure nearly equal thereto when the gaseous sample is introduced via the gaseous sample introduction piping 22 and a high voltage is applied between the extraction electrode 42 and the needle electrode 44 by the corona discharge power supply 30. The ionized gaseous sample is introduced through the pores 46, 48, 38 and 40 to the analyzer 28c, where its mass is analyzed.

The analyzer 28c is constituted of an ion pool-type ion trap mass spectrometer to detect whether the gaseous sample contains a hazardous material, for example, a nitro compound having a nitro group, which has a very low saturated vapor pressure and is difficult to detect. It is to be noted that the analyzer 28c may come in any other analyzer such as a quadruple mass spectrometer, a magnetic sector-type mass spectrometer, or a gas chromatograph.

The analyzer 28c is constituted as mass analysis means to detect a molecular weight as mass of the ionized gaseous sample and output this molecular weight as an analysis result to the data processor 24. The data processor 24 is constituted as decision means to collate the molecular weight output from the analyzer 28c and a molecular weight of the nitro compound with each other to decide whether they agree, that is, whether the gaseous sample contains the hazardous material and then output a decision result onto a screen.

Further, in the present embodiment, the needle electrode 44 and the extraction electrode 42 are provided with an ammeter and a voltmeter (neither of which is shown) to detect a current and a voltage respectively in order to detect conditions of the needle electrode 44 and the extraction electrode 42, that is, whether foreign matter such as Si or C is stuck to the needle electrode 44 or the extraction electrode 42 in connection with ionization, so that detection outputs of the ammeter and the voltmeter are provided to the data processor 24.

In this configuration, when the test sample 10 enters the X-ray inspection region of the X-ray inspection device 14 as the belt conveyor 12 moves, a detection signal is output from the entrance side sensor 18a to turn on the corona discharge power supply 30, which causes the corona discharge section 36 to initiate corona discharge. Simultaneously, vapor generated from the test sample 10 is sucked and introduced as the gaseous sample to the hazardous material detection device 16. If a high voltage is applied between the extraction electrode 42 and the needle electrode 44 by the corona discharge power supply 30 when the gaseous sample is introduced to the corona discharge section 36, corona discharge occurs in the corona discharge region 36a between the extraction electrode 42 and the needle electrode 44, to ionize the gaseous sample. The ionized gaseous sample is introduced to the analyzer 28c, where its mass is detected. When an analysis result from the analyzer 28c is transmitted to the data processor 24, the data processor 24 decides whether a molecular weight obtained as a result of the analysis agrees with the molecular weight of the hazardous material. If the molecular weight obtained as a result of the analysis agrees with the molecular weight of the hazardous material, that is, if a vapor of the hazardous material is detected, the process goes to detailed inspection.

If the molecular weight obtained as a result of the analysis does not agree with the molecular weight of the hazardous material, on the other hand, the result is displayed on a display screen of the data processor 24. Then, if the test sample 10 goes out of the X-ray inspection region, the detection signal is output from the exit side sensor 18b, to turn off the corona discharge power supply 30, thereby terminating inspection of the test sample 10. A time required by the test sample 10 to pass through the X-ray inspection region is set to, for example, 15 seconds or so, so that in about 15 seconds after the corona discharge power supply 30 is turned on, the corona discharge power supply 30 is turned off.

In such a manner, in the present embodiment, since the detection signal output from the entrance side sensor 18a is used as the instruction in response to which the corona discharge power supply 30 is held ON only for a constant time, to ionize the gaseous sample only for a set time, the corona discharge power supply 30 need not always be held ON, so that it is possible to suppress Si or C from sticking to the needle electrode 44 and the extraction electrode 42 and also to continuously operate the system for a long time, thereby contributing to a prolonged service life of each of the electrodes.

Although the embodiment has been described with reference to such an example that the corona discharge power supply 30 is turned on or off in accordance with the detection signals from the sensors 18a and 18b, if the test sample 10 is conveyed only in a certain time zone, an operator may operate the data processor 24 such that the corona discharge power supply 30 can be held ON only for a certain time zone.

Figure 3:
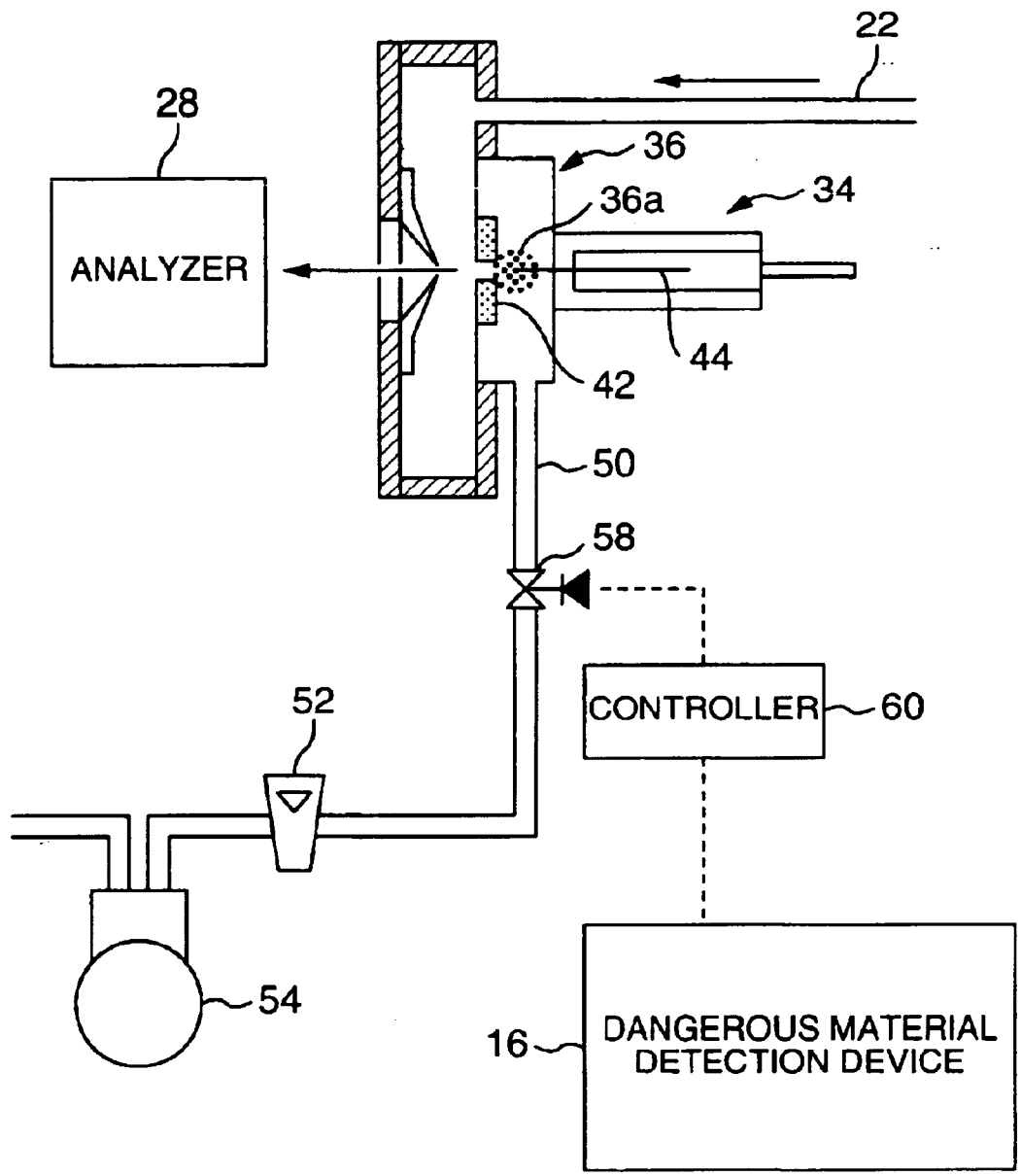
FIG. 3 is an important part configuration diagram showing a second embodiment of a hazardous material detection system related to the invention.

The following will describe a second embodiment of a hazardous material detection system related to the invention with reference to FIG. 3.

According to the present embodiment, in the middle of a conduit of a flow piping 50 is there provided an electromagnetic valve 58 which is connected via a controller 60 to a hazardous material detection device 16, so that if a detection signal is output from an entrance side sensor 18a, this detection signal is output to a controller 60, which in turn generates a control signal, in accordance with which the electromagnetic valve 58 is opened only for a constant time but held closed for the other times, with the other components being the same as those of FIG. 1.

In the present embodiment, when a test sample 10 is conveyed as a belt conveyor 12 moves and detected by an entrance side sensor 18a, in response to the detection signal of the sensor 18a, the controller 60 outputs the control signal to an electromagnetic valve 58 to open it only for the constant time, so that as a gaseous sample introduction pump 54 operates, a gaseous sample is introduced from gaseous sample introduction piping 22 into an ion source section 34 only for the constant time. The gaseous sample thus introduced is ionized at a corona discharge section 36 and analyzed at an analyzer 28, so that an analysis result is displayed on a screen of a data processor When the test sample 10 passes through an X-ray inspection device 14 and goes out of an X-ray inspection region, an exit side sensor 18b outputs the detection signal, so that when this detection signal is input to a controller 60, the control signal output from the controller 60 is turned off to close the electromagnetic valve 58 in order to stop introduction of the gaseous sample to the ion source section 34, while simultaneously a corona discharge power supply 30 is turned off, to terminate inspection on the test sample 10.

In the present embodiment, since the gaseous sample is introduced into the in source section 34 only for the time of inspecting the test sample 10, it is possible to more effectively suppress foreign matter contained in the gaseous sample from sticking to a needle electrode 44 or a extraction electrode 42, thereby prolonging a service life of each of the electrodes. In this case also, the corona discharge power supply 30 is turned off only for the time of inspection of the test sample 10, so that occurrence of contamination due to ionization can be suppressed more effectively than in the case of ionizing the gaseous sample all the time, thereby prolonging the service life of a system.

Further, in the present embodiment, a flow rate of the gaseous sample flowing through the flow piping 50 is controlled by opening and closing the electromagnetic valve 58 and so can be controlled in a moment of time.

Figure 4:
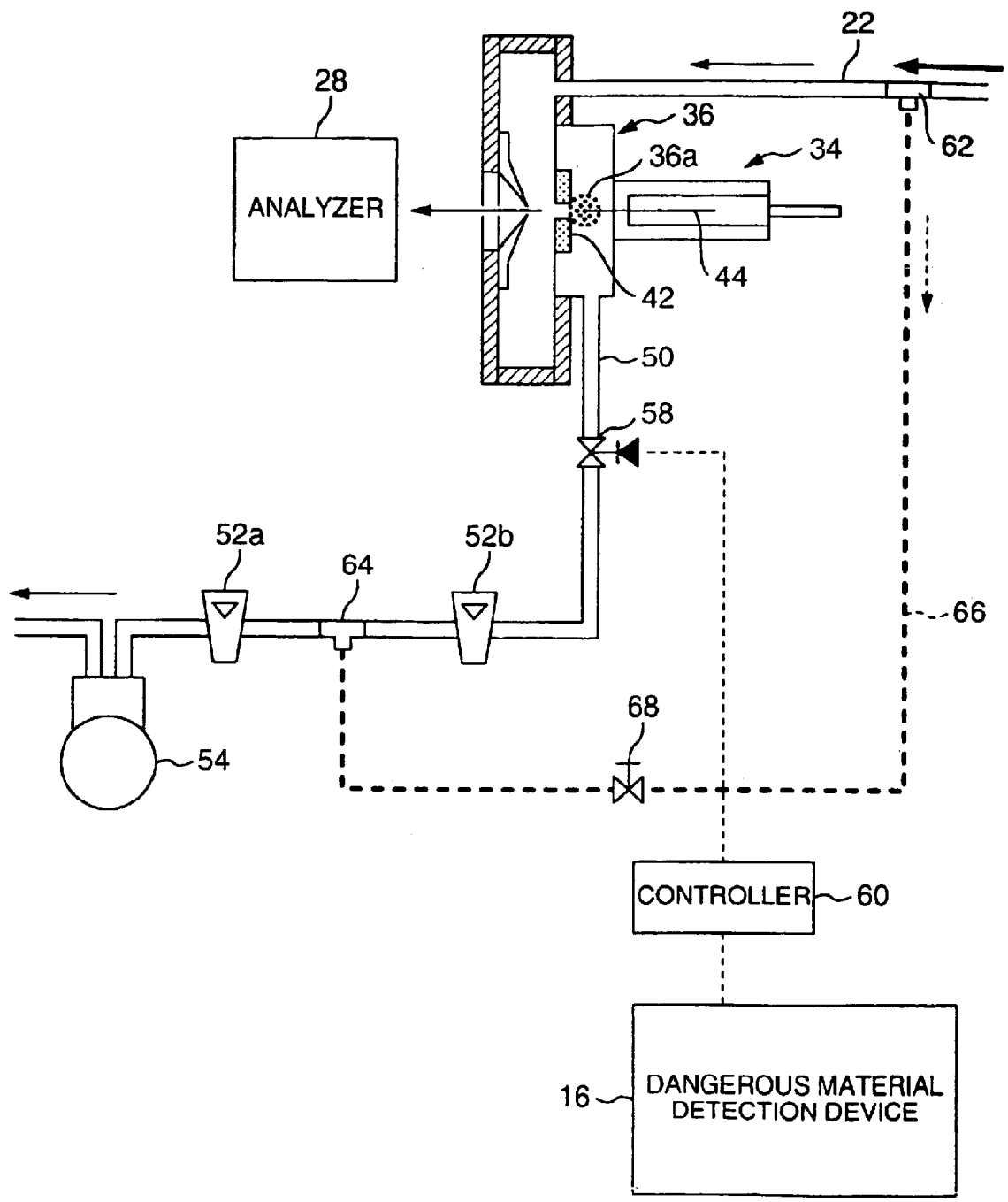
FIG. 4 is an important part configuration diagram showing a third embodiment of a hazardous material detection system related to the invention.

The following will describe a third embodiment of a hazardous material detection system related to the invention with reference to FIG. 4. The present embodiment has such a configuration that in the middle of a conduit of gaseous sample introduction piping 22 there is inserted a union T-tube (Y-form joint) 62, while a union T-tube 64 is inserted in such a region of flow piping 50 as to be on a downstream side of an electromagnetic valve 58. The T-tubes 62 and 64 are connected to a gaseous sample introduction piping 22 serving as a main path connected to an ion source section 34 and also interconnected with a bypass path 66. In the middle of bypass path 66 there is inserted an electromagnetic valve 68 which is opened all the time to set a flow rate of a gaseous sample flowing through the bypass path 66 larger than that of the gaseous sample flowing through the main path, with the other components being the same as those of FIG. 3.

When the gaseous sample is introduced to the ion source section 34 by opening/closing the electromagnetic valve 58, the rapid opening/closing operation of the electromagnetic valve 58 may cause corona discharge to become unstable due to a rapid variation in flow rate for a moment. If the corona discharge becomes unstable, it has an influence on analysis of the ionized gaseous sample, thereby giving rise to a detection mistake. Further, since it is required to detect whether a test sample contains a hazardous material in a short period of time, it is not desirable that a decrease in flow rate of the gaseous sample introduced to the ion source section 34 decreases a detection speed.

Therefore, as in the case of the present embodiment, the bypass path 66 is provided so that the flow rate of the gaseous sample flowing through the bypass path 66 may be larger than that of the gaseous sample introduced to the ion source section 34. It is, therefore, possible to suppress the influence on the corona discharge without decreasing an entire flow rate, thereby sucking in the large quantity of gaseous sample in a short lapse of time to inspect it in a short lapse of time.

According to the present embodiment also, to turn on/off the electromagnetic valve 58, an operator can control on opening/closing of the electromagnetic valve 58.

In the present embodiment, since the gaseous sample is introduced into the in source section 34 only for the time of inspection of the test sample 10, it is possible to more effectively suppress foreign matter contained in the gaseous sample from sticking to a needle electrode 44 or a extraction electrode 42, thereby prolonging a service life of each of the electrodes. Further, a corona discharge power supply 30 is turned off only for the time of inspection of the test sample 10, so that occurrence of contamination due to ionization can be suppressed more effectively than in the case of ionizing the gaseous sample all the time, thereby prolonging the service life of a system.

Furthermore, it is possible to suck in the large quantity of gaseous sample in a short lapse of time to inspect it in a short lapse of time without having an adverse effect on the corona discharge.

Figure 5A:
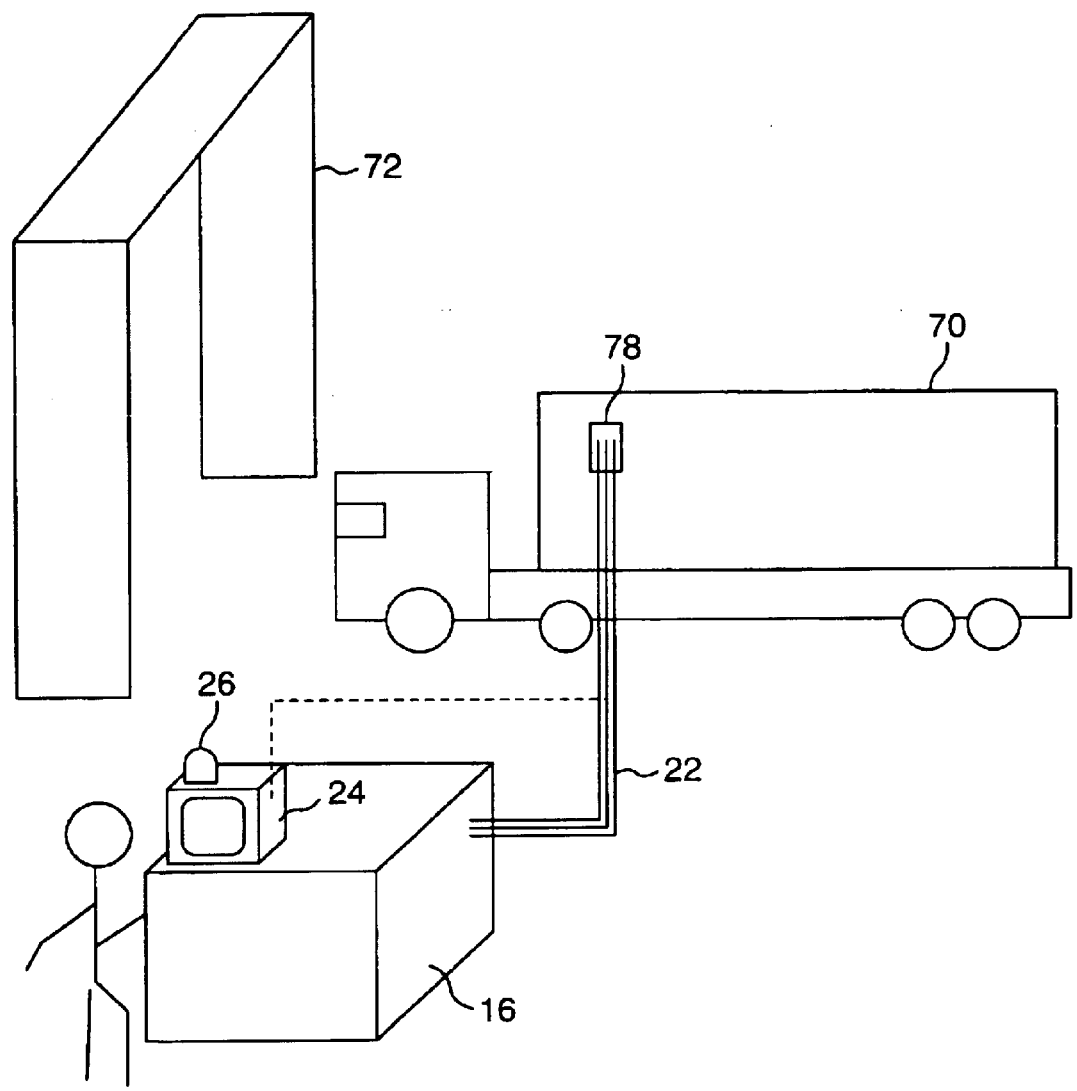
FIG. 5A is an overall configuration diagram showing a fourth embodiment of a hazardous material detection system related to the invention.
Figure 5B:
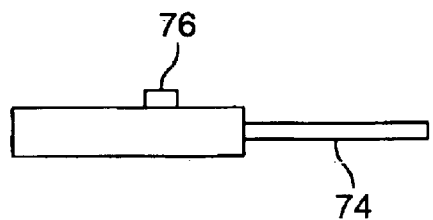
FIG. 5B is a configuration diagram of an analysis probe.

The following will describe a fourth embodiment of a hazardous material detection system related to the invention with reference to FIGS. 5A and 5B.

The present embodiment is arranged as a system for detecting an atmospheric gas in a container 70 mounted on a heavy truck, in which a hazardous material detection device 16 detects whether a hazardous material is contained in the atmospheric gas in the container 70 before the container 70 comes in a large-size X-ray inspection device 72 and also which has such a configuration that a gaseous sample introduction piping 22 is mounted at its tip with an analysis probe 74 in place of arranging a sucking section 20, which analysis probe 74 is provided with a changing-over switch in place of sensors 18a and 18b, with the other components being the same as those of FIG. 1.

In the present embodiment, in an airport or other public facilities, in inspection of the container 70 etc. loaded on a heavy truck, when an examiner inserts the tip side of the probe 74 into an opening 78 formed in the container 70 and also turns on the changing-over switch 76, a gaseous sample introduction pump 54 operates to introduce the atmospheric gas in the container 70 as the gaseous sample in order to initiate corona discharge on the introduced gaseous sample, so that the ionized gaseous sample is analyzed by an analyzer 28c and a result of this analysis is displayed on a screen of a data processor 24.

When the examiner turns off the changing-over switch 76, a corona discharge power supply 30 is turned off, to stop the corona discharge at an ion power supply section 34.

In the present embodiment, corona discharge is initiated only when the changing-over switch 76 is operated to turn on the corona discharge power supply 30, so that occurrence of contamination due to ionization can be suppressed more effectively than in the case of ionizing the gaseous sample all the time, thereby prolonging the service life of each electrode.

Further, in the present embodiment, when the container 70 is not to be inspected, the changing-over switch 76 is operated to stop introduction of the gaseous sample, so that salt contents or water droplets, even if contained in a large-scale cargo such as the container 70, can be prevented from being introduced always, thereby preventing a needle electrode 44 or a extraction electrode 42 from being contaminated by foreign matter.

In the present embodiment, as in the case of baggage inspection, if any suspicious material undeclared is found in the container 70 by the large-size X-ray inspection device 72, the examiner can also insert the probe 74 into the opening 78 and turn on the changing-over switch 76, to introduce the atmospheric gas in the container 70 and also initiate corona discharge. If no vapor of a hazardous material is detected by this inspection, he can also pull out the probe 74 from the opening 78 and permit passage of the container 70. If the vapor of the hazardous material is detected, the container 70 is inspected in detail.

Although the present embodiment has been described with reference to a case where the examiner turns on/off the changing-over switch 76, an operator may operate a data processor 2 to set a time when the atmospheric gas in the container 70 is to be introduced or a time when corona discharge is to be initiated. Further, the changing-over switch 76 may be of such a configuration that it is turned on and off automatically when the examiner inserts the probe 74 into the opening 78 and when he pulls out the probe 74 from the opening 78 respectively.

Figure 6A:
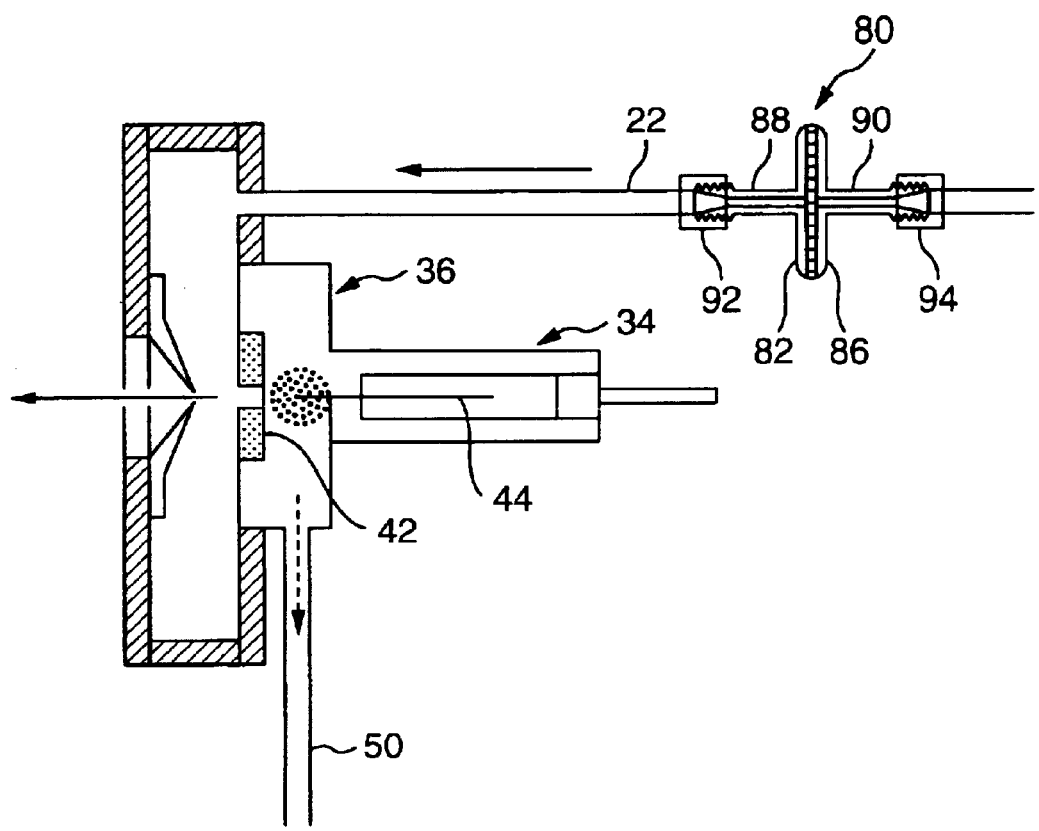
FIG. 6A is an important part configuration diagram showing a fifth embodiment of a hazardous material detection system related to the invention.
Figure 6B:
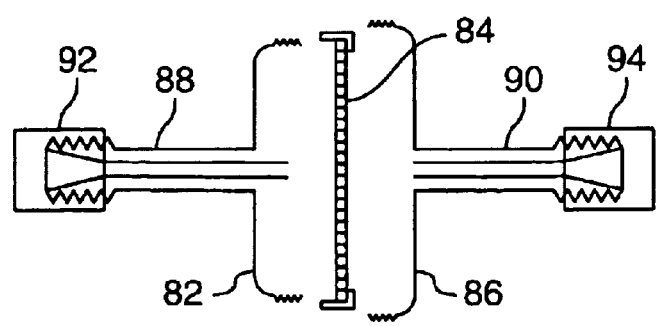
FIG. 6B is an exploded important part configuration diagram of a filter unit.

The following will describe a fifth embodiment of a hazardous material detection system related to the invention with reference to FIGS. 6A and 6B. The present embodiment has such a configuration that a filter unit 80 for collecting dusts and organic substances contained in a gaseous sample is provided partway along a conduit of gaseous sample introduction piping 22, with the other components being the same as those of the preceding embodiments.

The filter unit 80 comprises a tube body 82, a disk-type filter 84 fixed on the side of an opening of the tube body 82, a tube body 86 coupled as twisted on the side of an outer periphery of the tube body 82, a pipe 88 connected to one end of the tube body 82, and a pipe 90 connected to one end of the tube body 86 in such a configuration that the pipe 88 and 90 are linked to the gaseous sample introduction piping 22 via joints 92 and 94 respectively.

In the present embodiment, since the filter unit 80 is provided partway along the conduit of the gaseous sample introduction piping 22 to collect the dusts and organic substances contained in the gaseous sample, it is possible to suppress the dusts and organic substances from entering an ion source section 34, thereby more effectively preventing foreign matter from sticking to a extraction electrode 42 or a needle electrode 44.

Further, the filter unit 80 can be replaced readily by providing it with a mechanism for heating it when the filter unit 80 is provided at a portion partway along the gaseous sample introduction piping 22 and if this portion may possibly become a cold spot or by employing such a construction that only the filter unit 80 can be replaced through in one-touch operation.

According to the present embodiment, in the filter unit 80, such a disk-type filter 84 as to have a large area and a small thickness is used, so that by providing this filter unit 80, it is possible to suppress a detection speed from being decreased.

Further, since the filter unit 80 is linked via the joints 92 and 94 to the gaseous sample introduction piping 22, it can be replaced easily. Further, by mounting a heater in a periphery of the joints 92 and 94 or winding a heat insulating material around them to keep them warm, it is also possible to prevent the gaseous sample from being absorbed to the joints 92 and 94.

Figure 7:
FIG. 7 is an explanatory waveform chart of a measurement result obtained when a needle electrode is contaminated.

In these embodiments, in a process of inspecting a test sample 10 or a container 70, a voltage and a current of a needle electrode 44 are sequentially measured, a result of the measurement is monitored by a data processor, a result of the monitoring is in turn displayed on a screen of the data processor 24 as shown in FIG. 7. If at least one of the voltage and current of the needle electrode 44 exceeds an alarm set value, an alarm unit 26 can generate an alarm, thereby prompting cleaning.

As described above, by the invention, the gaseous sample is ionized only when necessary, to make it possible to suppress occurrence of contamination due to ionization more effectively than in the case of ionizing the gaseous sample all the time, thereby prolonging a service life of a system.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A hazardous material detection system comprising:
   gaseous sample introduction means for introducing a gaseous sample containing a substance stuck to a detection object;
   ionization means for ionizing the gaseous sample introduced by the gaseous sample introduction means, in response to an instruction;
   mass analysis means for analyzing mass of the gaseous sample ionized by the ionization means; and
   decision means for deciding whether the gaseous sample contains a hazardous material, based on an analysis result from the mass analysis means,
   wherein the ionization means ionizes the gaseous sample only for a time specified by the instruction.

2. A hazardous material detection system according to claim 1, wherein:
   the gaseous sample introduction means is provided with a main path which introduces the gaseous sample from the detection object to the ionization means and a bypass path which discharges the gaseous sample from the detection object as bypassing the ionization means; and
   a flow rate of the gaseous sample passing through the bypass path is set larger than a flow rate of the gaseous sample passing through the main path.

3. A hazardous material detection system according to claim 2, wherein a filter unit which collects dust and organic substances contained in a fluid flowing through the main path is mounted to the main path on an upstream side of the ionization means.

4. A hazardous material detection system according to claim 1, further including a sensor, said sensor being disposed for sensing proximity of said detection object, whereby when said sensor detects said detection object, said sensor outputs a detection signal which generates said instruction for controlling said ionization means.

5. A hazardous material detection system according to claim 1, further including a sensor, said sensor being disposed for sensing proximity of said detection object, whereby when said sensor detects said detection object, said sensor outputs a detection signal which generates a control signal for causing said gaseous sample introduction means to introduce a gaseous sample.

6. A hazardous material detection system according to claim 1, wherein said gaseous sample introduction means includes a bypass path, and a valve for controlling flow through said bypass path, said valve being controlled in response to a detection signal generated by a sensor disposed for sensing proximity of said detection object.

7. A hazardous material detection system according to claim 1, wherein said ionization means is a corona discharge means.

8. A hazardous material detection system comprising:

gaseous sample introduction means for introducing a gaseous sample containing a substance stuck to a detection object, in response to a control signal;

ionization means for ionizing the introduced gaseous sample only in the case where the gaseous sample has been introduced by the gaseous sample introduction means and, in the other cases, stopping ionization of the introduced gaseous sample;

mass analysis means for analyzing mass of the gaseous sample ionized by the ionization means; and decision means for deciding whether the gaseous sample contains a hazardous material, based on an analysis result from the mass analysis means.

9. A hazardous material detection system according to claim 8, wherein the gaseous sample introduction means is provided with a main path which introduces the gaseous sample from the detection object to the ionization means and a bypass path which discharges the gaseous sample from the detection object as bypassing the ionization means; and a flow rate of the gaseous sample passing through the bypass path is set larger than a flow rate of the gaseous sample passing through the main path.

10. A hazardous material detection system according to claim 9, wherein a filter unit which collects dust and organic substances contained in a fluid flowing through the main path is mounted to the main path on an upstream side of the ionization means.

11. A hazardous material detection system according to claim 8, further including a sensor, said sensor being disposed for sensing proximity of said detection object, whereby when said sensor detects said detection object, said sensor outputs a detection signal which generates an instruction for controlling operation of said ionization means.

12. A hazardous material detection system according to claim 8, further including a sensor, said sensor being disposed for sensing proximity of said detection object, whereby when said sensor detects said detection object, said sensor outputs a detection signal which generates said control signal for causing said gaseous sample introduction means to introduce a gaseous sample.

13. A hazardous material detection system according to claim 8, wherein said gaseous sample introduction means includes a bypass path, and a valve for controlling flow through said bypass path, said valve being controlled in response to a detection signal generated by a sensor disposed for sensing proximity of said detection object.

14. A hazardous material detection system according to claim 8, wherein said ionization means is a corona discharge means.

15. A hazardous material detection system comprising:

a corona discharge section capable of ionizing a gaseous sample, said gaseous sample being taken in proximity to a detection object;

an analyzer for analyzing the gaseous sample ionized by the corona discharge section; and a data processor for deciding whether the gaseous sample contains a hazardous material, based on an analysis result from the analyzer, wherein, when said gaseous sample is introduced into said corona discharge section, the gaseous sample is ionized for a specified period of time in response to an instruction.

16. A hazardous material detection system according to claim 15, further including a sensor, said sensor being disposed for sensing proximity of said detection object, whereby when said sensor detects said detection object, said sensor outputs a detection signal which generates said instruction for ionizing said gaseous sample.

17. A hazardous material detection system according to claim 15, further including a sensor, said sensor being disposed for sensing proximity of said detection object, whereby when said sensor detects said detection object, said sensor outputs a detection signal which generates a control signal for causing said gaseous sample to be introduced to said corona discharge section.

18. A hazardous material detection system according to claim 15, wherein a gaseous sample introduction means is provided, said gaseous sample introduction means having a main path which introduces the gaseous sample from the detection object to the ionization means and a bypass path which discharges the gaseous sample from the detection object as bypassing the ionization means; and a flow rate of the gaseous sample passing through the bypass path is set larger than a flow rate of the gaseous sample passing through the main path.

19. A hazardous material detection system according to claim 18, wherein a filter unit which collects dust and organic substances contained in a fluid flowing through the main path is mounted to the main path on an upstream side of the ionization means.

20. A hazardous material detection system according to claim 18, wherein said bypass path includes a valve for controlling flow through said bypass path, said valve being controlled in response to a detection signal generated by a sensor disposed for sensing proximity of said detection object.

* * * * *